Figure 1:
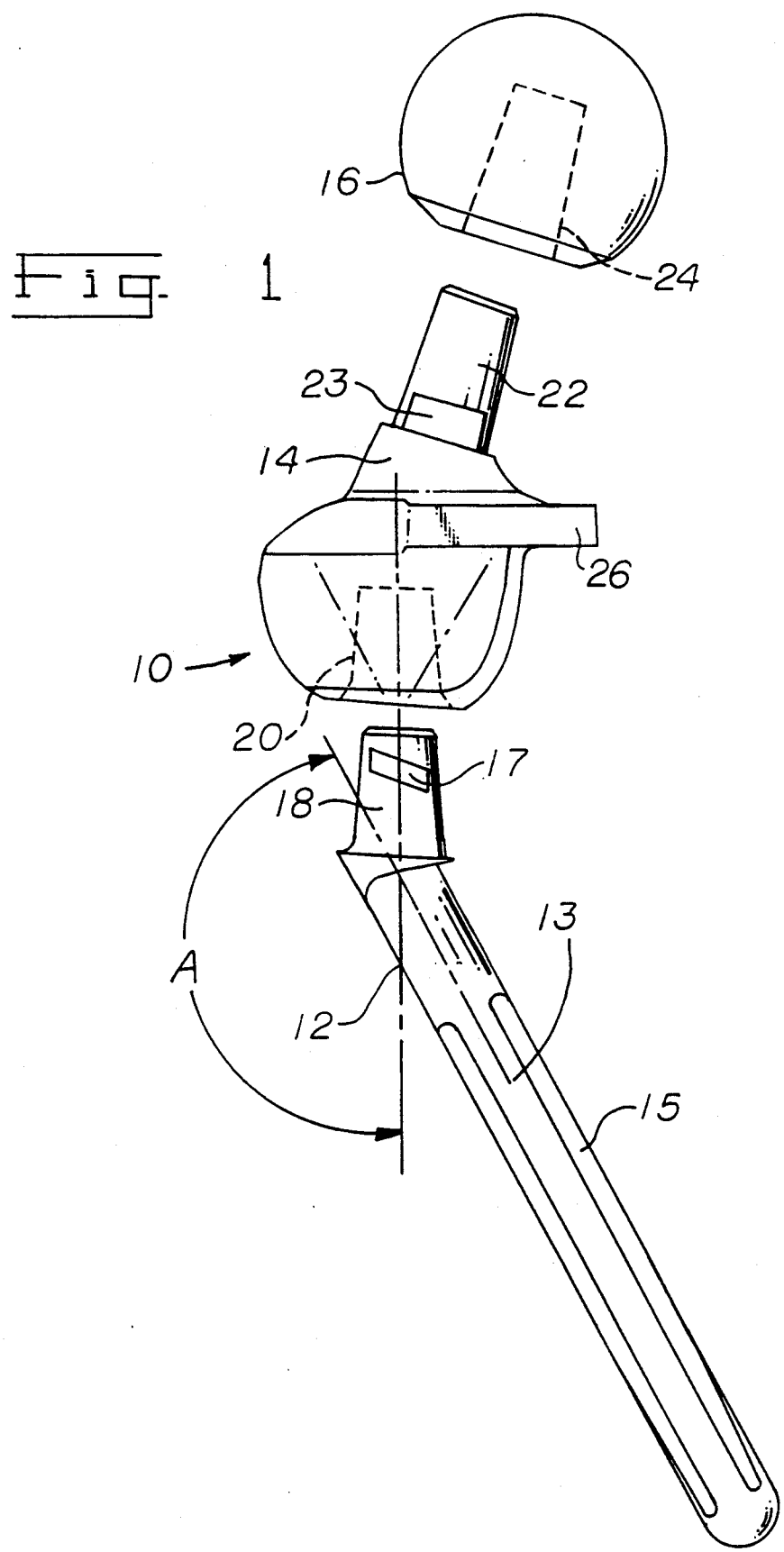

United States Patent [19]
Paxson et al.

[11] Patent Number: 5,135,529
[45] Date of Patent: Aug. 4, 1992

[54] INSTRUMENT FOR IMPLANTING MODULAR HIP JOINT PROSTHESIS WITH ADJUSTABLE ANTEVERSION AND METHOD OF USING SAID INSTRUMENT

[75] Inventors: Robert D. Paxson, Cockeysville, Md.; Carl M. Stamp, Cordova, Tenn.

[73] Assignee: Dow Corning Wright Corporation, Arlington, Tenn.

[21] Appl. No.: 608,762

[22] Filed: Oct. 31, 1990

Related U.S. Application Data

[62] Division of Ser. No. 431,412, Nov. 3, 1989, Pat. No. 5,002,581.

[51] Int. Cl.$^5$ ............................................. A61F 5/04
[52] U.S. Cl. ........................................ 606/85; 623/23
[58] Field of Search .................. 623/16, 18, 22, 23; 606/79, 80, 82, 85, 86

[56] References Cited

U.S. PATENT DOCUMENTS

| | | |
|---|---|---|
| 4,551,863 | 11/1985 | Murray .................................. 623/23 |
| 4,601,289 | 7/1986 | Chiarizzio et al. .................... 623/23 |
| 4,765,328 | 8/1988 | Keller et al. .......................... 623/28 |

*Primary Examiner*—David Isabella
*Attorney, Agent, or Firm*—John L. Chiatalas

[57] ABSTRACT

The present invention provides a modular hip prosthesis, and instrumentation for implanting the same, which has provision for varying the angulation between the stem portion and the trochanteral module portion by provision of connection means between the neck and stem which can be positioned or attached together in a variety of rotational positions. Variation of the angulation or anteversion is made possible in accordance with the present invention by virtue of the fact that the axis of the connection portion of the stem and neck is angularly offset from the axis of the body of the stem and neck, respectively. A further aspect of this invention is the provision of instrumention for formation of a cavity for implantation of a prosthesis of this invention which is provided with indication means for indicating to the surgeon the optimum angle for assembly of the prosthesis of invention for implantation into a particular proximal femur.

7 Claims, 4 Drawing Sheets

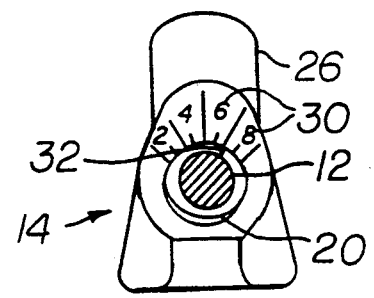
Fig. 3
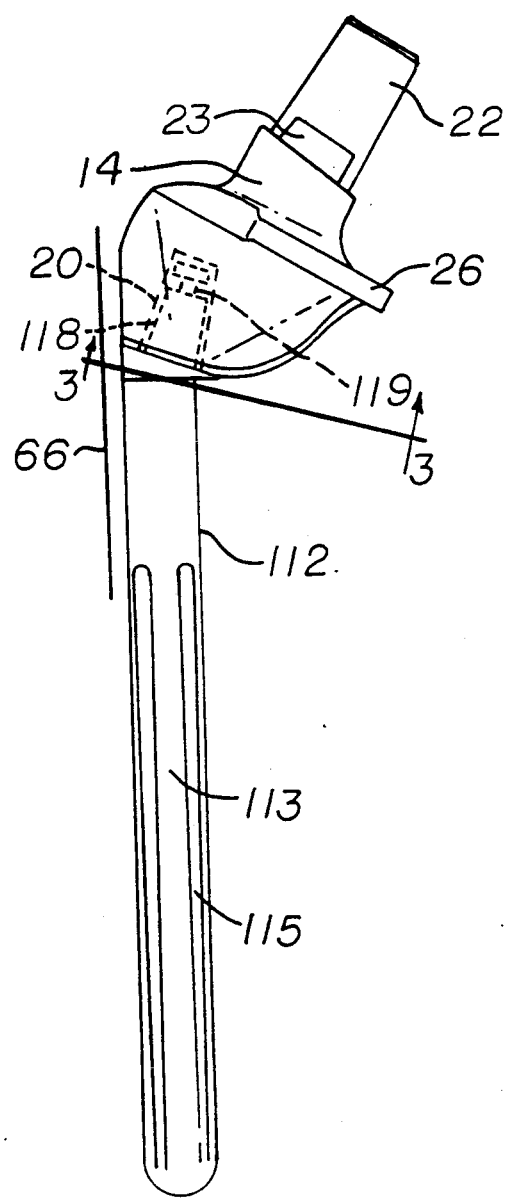
Fig. 2
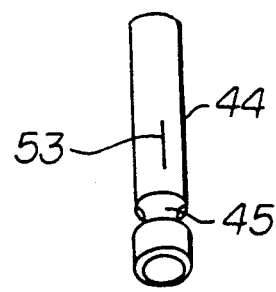
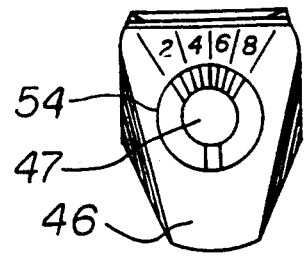
Fig. 6

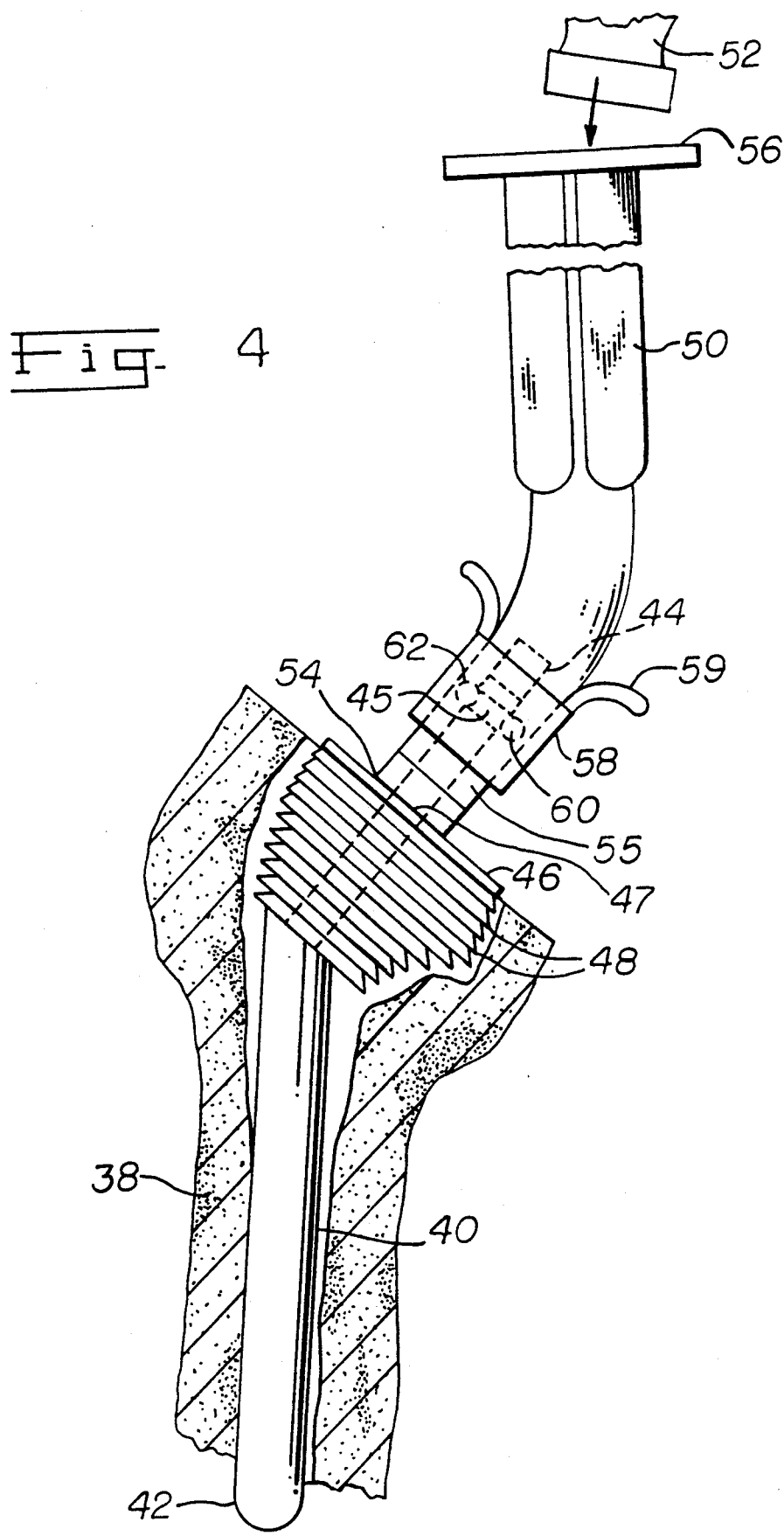

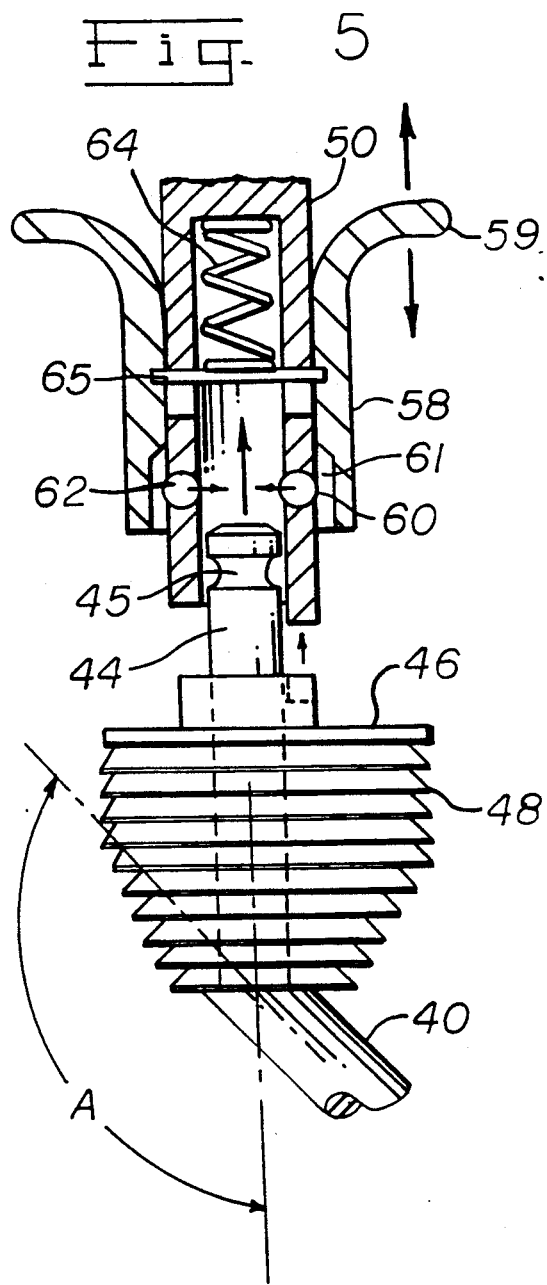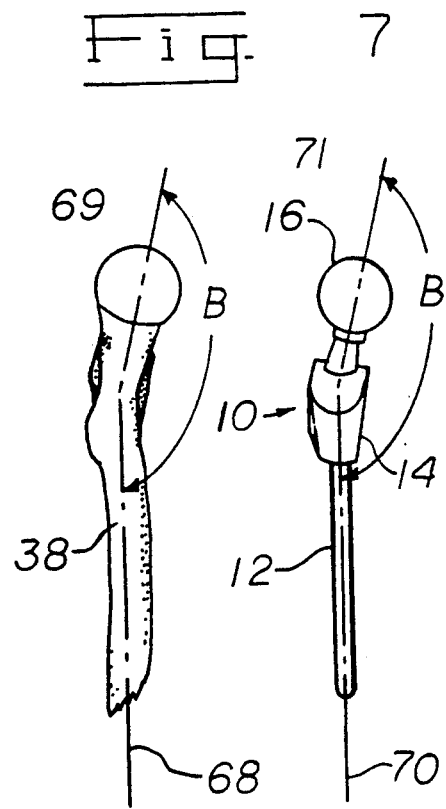

INSTRUMENT FOR IMPLANTING MODULAR HIP JOINT PROSTHESIS WITH ADJUSTABLE ANTEVERSION AND METHOD OF USING SAID INSTRUMENT

This is a divisional of copending application Ser. No. 07/431,412 filed on Nov. 3, 1989, now U.S. Pat. No. 5,002,581.

BACKGROUND OF THE INVENTION

1. Field of the Invention

This invention relates to artificial joints and particularly to modular proximal femoral hip prostheses, and a method and instrumentation for implantation of the same.

2. Description of the Prior Art

Various prostheses have heretofore been designed to replace one or both components of a ball and socket hip joint. Generally the ball portion is connected to an arm composed of a neck and a stem or shaft which stem or shaft is embedded in the intramedullary canal of the proximal femur for hip reconstruction. Such prostheses are often formed with an integral stem and neck portion. Often a removable ball or head element is positioned on the proximal end of the neck. See, for example, U.S. Pat. Nos. 4,012,795 or 4,459,708.

Recently the use of modular structures fitted together from a number of replaceable parts available in a variety of sizes have been used. With such prostheses it is possible to replace either the head portion or trochanteral portion of the prostheses, or both, without removal of the stem from the bone cavity. U.S. Pat. Nos. 4,608,055, 4,676,797, and 4,693,724 are all illustrative of such devices. The latter patent also discloses the possibility that the angle at which the neck protrudes from the proximal end of the femur (referred to in said patent as "anteversion") may be adjusted without removal of the stem by pivoting the neck on the end of the implanted stem. None of the prior art devices of which applicant is aware provide any means for varying the angle between the axis of the trochanteral module and the axis of the stem so that the actual angulation (sometimes referred to as anteversion) or slope of the proximal end of the femur may be duplicated by adjustment of said angle.

The present invention provides a modular hip prosthesis and instrumentation for implanting the same, which has provision for varying the angulation between the stem portion and the trochanteral, or neck, portion by provision of connection means between the trochanteral module and stem which can be positioned or attached together in a variety of rotational positions. Variation of the angulation or anteversion is made possible in accordance with the present invention by virtue of the fact that the axis of the connection portion between the stem and trochanteral portion is angularly offset from the axis of the body of the stem. The prostheses of this invention are further characterized by the fact that no impediment exists to securing the stem and neck together in a variety of rotational positions. Like other modular prostheses the hip joint prostheses of this invention provide the advantage that either or both the ball component or trochanteral module component can be removed if replacement becomes necessary without extraction of the stem from the bone canal. Different size balls or trochanteral components could also be substituted should the surgeon decide that such revision is necessary after a period of time.

A further aspect of this invention is the provision of instrumentation for formation of a cavity for implantation of a prosthesis of this invention which is provided with indicia or markings for indicating to the surgeon the optimum angle for assembly of the prosthesis of invention for implantation into a particular proximal femur. The invention further provides a novel method for determining the proper angulation for a particular proximal femur using angulation readings taken off of indicia provided on the rasp used to prepare the proximal femur for the prosthesis. Such readings then provide a basis for assembly of the prosthesis in the correct orientation to fit the proximal femur.

Briefly summarized, the present invention provides a modular hip joint prosthesis having provision for varying the angulation of the stem portion and the trochanteral module to coincide with the degree of angulation in the proximal femur of a patient. The prosthesis includes a ball, a stem component for implantation in a proximal femur, a trochanteral module adapted to be connected at its proximal end to said ball and at its distal end to said stem component by a connection portion. The connection portions of the stem and trochanteral components have no mechanical impediment to limit securing the two components together in a variety of rotational positions. The trochanteral module component is of an oblong cross-section on a plane perpendicular to the longitudinal axis of its distal connection portion. It, further, is symmetrical in shape across the plane in which the axis of the ball connection shaft is located, but is preferably non-symmetric in all other planes. Thus when the stem component is rotated in different orientations relative to the trochanteral module, a tilting of the trochanteral module occurs relative to the stem, making it possible to closely match the natural tilt of the proximal femur. The stem component is provided with a connection portion which, as already noted, mates with the connection portion of the trochanteral module in a variety of rotational positions, with the axis of the connection portion of the stem being angularly offset from the axis of the body of the stem. The implant is provided with markings or indicia positioned circumferentially around the connection portion so that the surgeon can match the orientation of the implant with that of the instrumentation as observed from the indicia thereon when the rasp portion of the instrumentation is imbedded in the proximal femur.

The novel surgical instruments of this invention include a stem component which has a connection portion offset at an angle identical to the angle at which the connection portion of the implant stem is offset from the axis of the implant stem. The instrument connection portion is adapted to receive a series of rasp block portions of progressively increasing dimension. Each of the rasp block portions are of a shape corresponding to the trochanteral modules of the implants. The rasp blocks and the instrument connection portion each have markings thereon located circumferentially around the connection portion for determination of the relative orientation between the rasp block and the stem axis. The neck of the implant and connection portion of the implant stem have similar markings to allow the surgeon to assemble the implant in the same orientation as observed on the rasp instruments after they have been inserted in a manner and orientation deemed to be optimal by the surgeon.

The novel method of the invention is as follows: the surgeon begins by removing the head of the proximal femur this resection being a rough resection. The surgeon then inserts a starter reamer into the medullary canal of the femur and sequentially reams using reamers of progressively increasing diameters until he finds a reamer of the appropriate diameter which contacts the cortical bone. The reamers employed are cylindrical in shape and have helical or longitudinal flutes which cut the bone. Once the appropriate diameter for the distal stem is thus determined by means of the reaming, the surgeon selects that same diameter distal trial stem and assembles onto it a proximal rasp portion which mimics the geometry of the trochanter module of the actual implant. The distal trial stem also corresponds to the geometry of the distal stem of the implant. The proximal rasp has a hole through it that has a center line that is coincident in orientation to the center line of the connection portion on the actual proximal wedge of the implant. The trial stem has a long cylindrical stud that projects proximally off of the distal stem at an angle that is the same angle as the connection portion on the actual distal stem, but this stud is cylindrical and has a length sufficient such that when assembled through the hole in the proximal rasp, the stud extends out of the other side of the proximal rasp and is then attached to the driving handle. The driving handle holds the entire assembly together by engaging the end of the stud on the trial stem by means of an interlock mechanism. The entire assembly is locked together such that the proximal rasp can rotate on the distal stem but is axially retained on the driving handle. The distal stem can freely rotate about the center line of the stud axis, and the handle and proximal rasp may be locked together so that they rotate as one unit. Since the surgeon has already selected the distal trial stem by reaming, the only component that is changed during the sequential rasping is the proximal rasp. The surgeon begins with a small proximal rasp and progressively utilizes larger rasps until he determines the size which will best fit the proximal region of the bone. During the rasping process the surgeon is free to rotate the proximal rasp relative to the distal stem and thus determine an optimum orientation of the rasp. He will visualize the best position for the proximal rasp each time he drives the proximal rasp down into the bone. When he finally reaches the appropriate size rasp he will leave the rasp and distal stem in the bone but detach the driving handle so that he can see the top surface of the rasp and the stud projecting out through the hole in the rasp. The stud is provided with a line or other mark and the top surface of each rasp adjacent the opening is provided with a series of lines or marks. Each of these lines will be at approximately 11½ (or some other selected interval) apart from each other to indicate to the surgeon the orientation of the rasp on the rasp stem. The implant trochanteral module and implant stem are provided with identical markings so that the surgeon is able to assemble them in an orientation identical to that which was observed between the rasp and rasp stem. Hence the amount of anteversion in the actual implant when it is assembled is the same as that which was determined by virtue of the rasping procedure. The lines on both the rasp and implant neck are marked with letters or numbers, for example, 1 through 9 or A through J, etc. The surgeon thus can observe the designated orientation of the rasp and distal trial stem and assemble the prosthesis using the markings as a guide. The surgeon will thus assemble the distal stem onto the proximal wedge in the same position that was read off of the instrumentation, thereby insuring that the amount of angulation in the femoral implant is the same as the amount of angulation in the bone.

DRAWINGS

The invention will be explained more particularly with reference to the accompanying drawings wherein FIG. 1 is an elevational side view of a prosthesis of the present invention with the modular components detached from one another, FIG. 2 is a side view of another embodiment showing a trochanteral module assembled to a stem, FIG. 3 is a cross sectional view of the prosthesis of FIG. 2 taken along line 3—3, FIG. 4 is a side view of instrumentation for preparing a proximal femur for implantation of a prosthesis of this invention with a broken away femur shown in cross section and with other components broken away, FIG. 5 shows the connection portion of the instrumentation in FIG. 4 with parts broken away and with the handle portion shown in cross section, FIG. 6 is a top view of the rasp shown in FIGS. 4 and 5 with a trial stem having a marking thereon used in conjunction with said rasp shown removed therefrom with an end broken away, and, FIG. 7 is a prospective view showing a typical proximal femur and a prosthesis of this invention in a side by side relationship illustrating the version between the central and proximal parts of a femur and an implant for said femur.

Referring to the drawings there is seen in FIG. 1 a hip prosthesis 10 which consists of a stem component 12 a trochanteral module 14 and a ball or head portion 16. Stem 12 and module 14 are adapted to be connected together be means of male taper connection 18 and a mating female taper connection 20, preferably of the Morse taper type. Head 16 is similarly connected to neck portion 14 by means of friction fit tapers 22 and 24. A pair of notches 23 or similar means is provided on trochanteral module 14 to permit removal of the module from stem 12 if revision of the implant becomes necessary. Module 14 may be provided with a shoulder 26, which is intended to rest on the end of the resected femur. A shoulder 26 is generally provided on at least the medial side of the implant. Stem 12 is provided with a lower elongated portion 13 which is offset angularly from connection portion 18. Flutes or indentations 15 may optionally be provided in the implantable stem portion 13, to form channels for receiving bone cement or macro bone ingrowth. An extraction groove 17 is provided to facilitate removal of the stem should it become necessary.

In the embodiment of FIG. 2 trochanteral module 14 is depicted with a slightly differing configuration or outline in which the lateral aspect of said trochanteral component and a stem are parallel to an imaginary line 66. Stem 112 has a lower portion 113 and flutes 115 similar to those shown in FIG. 1. The Morse tapered cone 118 is provided with an alternative end configuration with a circling indentation 119 which provides an alternative means for the surgeon to grasp the end of the stem module for removal if necessary.

As seen in FIG. 3 the bottom surface of the trochanteral module is provided with markings 30 which indicate possible different rotational orientations, markings 30 being radially positioned around the circumference of the Morse taper opening 20. Stems 12 and 112 are provided with a single mark 32 which can be placed in alignment with a desired mark selected from among 30 on the trochanteral marking. Pairs of markings 30 and 32 thus provide an indication to the surgeon of the relative orientation between the parts.

As seen in FIG. 6, similar markings are present on the surface of rasp block 46 said markings being indicated by numeral 54. As seen in FIG. 4, a trial stem 40 having dimensions similar to implant stem 13 is placed in the intramedullary canal of proximal femur 38 after resection of the proximal femur and drilling and reaming of the intramedullary canal to open the cavity of sufficient diameter and depth to accommodate the trial stem 40, which generally has a rounded lower end 42 to promote ease of insertion. Rasp wedge 46 is provided with cutting teeth 48. As already noted, a series of rasp wedges 46 of increasing size are provided with the instrumentation. Each rasp wedge is provided with an opening to accommodate attachment stud 44 which is integral with trial stem 40. Attachment stud 44 is provided with a reference mark 53 best seen in FIG. 6 at the top of each rasp wedge 46 is imprinted a series of indicia 54 positioned circumferentially around a portion of opening 47. Indicia 54 coincide with the indicia 30 on the trochanteral module of the actual implant 14. As seen from FIGS. 2, 3, 4 and 6, indicia 30 on the implant are positioned on the medial side of the trochanteral module. The corresponding markings on the rasp are positioned on the lateral side of the rasp wedge 46. In this way the markings will coincide even though the markings on the implant are on the distal side of the trochanteral module while the markings on the rasp wedge are on the proximal side thereof. While this placement is preferred, it will be apparent to those skilled in the art that the markings could be placed medially on the rasp wedge and the order of reading of the numerals or indicia be reversed so that reading on the wedge would have to be from right to left and on the trochanteral module from left to right. However the arrangement shown in the drawings is preferred since it promotes ease of reading and minimization of error in reading and placement of the parts.

As previously noted each time the surgeon uses a progressively larger rasp wedge 46 to enlarge the opening in the proximal femur 38, he will use his professional judgement to align the rasp wedge radially around the attachment stem 44 to a position which in his judgement best approximates the opening in the femur which is of course determined by the version angle B of the femur as seen in FIG. 7. The angle B being the relative displacement between the axis of the body of the femur and that of the neck of the femur. Once the cortical bone has been removed by rasping to the surgeons satisfaction, rasp handle 50 is removed so that the relative position between marking 53 and indicia 54 is observable. The surgeon can then assemble the trochanteral module 14 onto implant stem 13 in a position matching the orientation observed between the attachment stud 44 and rasp wedge 46. In other words mark 32 is placed at the same position relative to indicia 30 as mark 53 was observed to be relative indicia 54.

As seen in FIG. 4, rasp handle 50 is provided for use in rasping the cancellous bone from femur 38. Rasp handle 50 has a flattened upper surface 56 against which a hammer 52 may be struck to cause teeth 48 to remove some of the cortical bone. The mechanism for releasably attaching rasp handle 50 to the attachment stud 44 of the trial stem 40 is best viewed in FIG. 5. As noted, an engagement groove 45 encircles attachment stud 44 near its end. Engagement groove 45 is adapted to receive balls 60 and 62 which are positioned in a sleeve portion of the distal end of the rasp handle 50 a slidable sleeve 58 encircles the distal end of the rasp handle as seen in FIGS. 4 and 5. The distal inner portion of sleeve 58 is provided with a portion of enlarged inner radius 61 which allows balls 60 and 62 to move radially outward when sleeve 58 is raised to the position shown in FIG. 5. Sleeve 58 is provided with outwardly projecting proximal end 59 to permit manual raising and lowering of sleeve 58. When sleeve 58 is in its lowered position shown on FIG. 4 the balls are forced into engagement groove 45 to couple rasp handle to attachment stud 44. Rasp handle 50 can easily be removed from attachment stud 44 by moving the sliding sleeve 58 upward thus allowing balls 60 and 62 to move outwardly out of the engagement groove 45. An internal spring or similar means 64 is provided to urge sleeve 58 into the locked position illustrated in FIG. 4. A pin 65 or similar surface for engagement of spring 64 is provided to enable transfer of the springs force to sleeve 58.

As seen in FIG. 7 the desirable orientation of implant 10 is such that the angle B between stem axis 70 and neck axis 71 is the same as angle B between the hip stem 68 and head 69. Such alignment is achieved by virtue of positioning achieved as indicated in FIG. 3.

While I have described certain specific embodiments of the invention for illustrative purposes, various modifications will be apparent to those skilled in the art which do not constitute departures from the spirit and scope of the invention as defined in the appended claims.

What is claimed is:

1. A surgical instrument for forming a cavity in the femur to implant a modular hip prosthesis, the instrumentation comprising:
   a stem configured for positioning in the medullary canal of the femur, including opposed proximal and distal ends defining a first axis;
   a handle located at the proximal end for surgical manipulation of the instrument;
   at least one rasp element with a surface adapted for cutting or abrading bone material within the medullary canal along a second axis which is angularly offset from the first axis at the same degree as corresponding modular components of the hip prosthesis;
   means for locking the handle and rasp together against rotational movement relative to one another, allowing both axial and torsional forces to be transmitted by the handle to the rasp;
   means for releasably connecting the handle to the stem with the rasp held therebetween, allowing axial but not torsional forces to be transmitted by the handle to the stem;
   means for indicating the relative rotational orientation of the stem and rasp once a desired amount of bone material is removed from within the medullary canal, allowing the surgeon to position the modular components of the prosthesis in substantially the same rotational orientation in the femur to match the natural angle of anteversion of the patient's femur; and
   means for axially driving the rasp into the proximal femur.

2. Instrumentation according to claim 1 wherein means for releasably connecting the stem and handle together further comprises a quick-disconnect coupling.

3. Instrumentation according to claim 2 wherein the quick-disconnect coupling includes radially movable stops carried in the handle which engage a groove in an attachment portion of the stem to releasably hold the handle thereon, permitting detachment of the handle from the stem when the stops are moved radially outwardly.

4. Instrumentation according to claim 3 wherein the stops comprise spherical metal balls.

5. Instrumentation according to claim 1 further comprising a series of rasp elements each of progressively increasing dimensions.

6. Instrumentation according to claim 5 wherein the indicating means further comprises physical markings on the stem and rasp, each of the series of rasp elements being provided with such markings.

7. A method of implanting a modular proximal femoral prosthesis comprising the steps of:

(a) resecting the head of the proximal femur;

(b) inserting a reamer into the medullary canal of the femur then, sequentially, inserting reamers of progressively increasing diameters into the canal until a reamer is inserted of an appropriate diameter which contacts the cortical bone of the femur;

(c) selecting a distal trial stem having a diameter matching that of the reamer and a proximal portion with a stud thereon;

(d) selecting a rasp element having a central opening, assembling the rasp onto the proximal end of the stem with the stud projecting through the opening, releasably connecting a driving handle over the end of the stud and locking the handle and rasp together against relative rotational motion so that the proximal rasp is rotatable on the distal stem but is axially retained thereon;

(e) rasping the medullary canal with the rasp and then, progressively, with larger rasps until the size which optimally fits the proximal region of the bone is determined;

(f) rotating each proximal rasp relative to the distal stem to determine an orientation of the rasp which optimally matches the orientation of the bone, then detaching the driving handle from the stem while observing the rotational orientation between the rasp and the stud using reference marks on the rasp and the stem;

(g) assembling an implantable trochanteral module and stem and locking them together in the same observed orientation as the rasp and trial stem, using similar markings provided thereon; and (h) inserting the assembled implant into the medullary canal.

* * * * *